US005526841A

United States Patent [19]
Detsch et al.

[11] Patent Number: 5,526,841
[45] Date of Patent: Jun. 18, 1996

[54] WATER LINE DECONTAMINATION SYSTEM

[76] Inventors: Steven G. Detsch, 4115 The Hill Rd., Bonita, Calif. 91902; Scott L. Preston, 1127 Fairoaks Ave., Arroyo Grande, Calif. 93420

[21] Appl. No.: 109,622

[22] Filed: Aug. 20, 1993

[51] Int. Cl.⁶ .............................. B08B 3/04; B08B 5/00; B08B 9/02
[52] U.S. Cl. ............................ 137/15; 134/30; 134/95.1; 134/95.2; 134/102.2; 134/102.3; 134/169 C; 134/171; 137/240; 222/148
[58] Field of Search ............................... 134/102, 166 C, 134/167 C, 169 C, 169 R, 26, 30, 94.1, 95.1, 95.2, 99.1, 100.1, 102.1, 102.2, 102.3, 171; 137/240, 241, 15; 222/148

[56] References Cited

U.S. PATENT DOCUMENTS

| | | | |
|---|---|---|---|
| 3,625,231 | 12/1971 | Littrell, Jr. | 134/102.1 |
| 3,650,678 | 3/1972 | Hansen | 137/241 |
| 3,811,408 | 5/1974 | Thompson | 134/166 C |
| 4,193,818 | 3/1980 | Young et al. | 134/102.1 |
| 4,502,614 | 3/1985 | Weiler et al. | 137/240 |
| 4,892,112 | 1/1990 | Knetsch | 137/240 |

OTHER PUBLICATIONS

Bagga, B. S. et al., *Dental Asepsis Review*, vol. 6, No. 1, Jan., 1985, 2 pages.
Martin, M. V., "The Significance of the Bacterial Contamination of Dental Unit Water System", *British Dental Journal*, 163: 152, Sep. 5, 1987, 1 page.
Mayo, John A. et al., "Bacterial Biofilm: A Source of Contamination in Dental Air–Water Syringes", *Clinical Preventive Dentistry*, vol. 12, No. 2, Jun.–Jul. 1990, pp. 13–20.
Whitehouse, R. L. S. et al., "Influence of Biofilms on Microbial Contamination in Dental Unit Water", *Journal of Dentistry*, 19:5, 1991, pp. 290–295.
Miller, Chris H., "Water Contamination", The Office Sterilization and Asepsis Procedures Research Foundation 1991 Annual Conference, Jun. 6–8, 1991, pp. 1–3.
"Question & Answer: Update on Legionellosis", *SciTech Dental*, 1992, 1 page.
Zinman, Edwin J., "Tip of the Iceberg", *JADA*, vol. 123, Aug., 1992, p. 15.
Lewis, David L. et al., "Cross-contamination Potential with Dental Equipment", *The Lancet*, vol. 340, Nov. 21, 1992, p. 1252.
The Steriline™ Cartridge brochure, SciTech Dental, Bellevue, Washington.

*Primary Examiner*—George L. Walton
*Attorney, Agent, or Firm*—Brown, Martin, Haller & McClain

[57] ABSTRACT

A water line decontamination unit has inlets for connection to a supply of irrigant liquid, a supply of disinfectant, and a pressurized gas supply, and an outlet for connection to a water line inlet. A valve assembly in the unit controls the supply of irrigant liquid, disinfectant and gas to the water line so that only one of the fluids is supplied to the water line at any one time. A manual selector allows an operator to select a run condition in which irrigant liquid is supplied to the water line, a flush condition in which disinfectant is supplied to the water line, and a purge condition in which gas is supplied to purge liquid from the water line.

35 Claims, 3 Drawing Sheets

WATER LINE DECONTAMINATION SYSTEM

BACKGROUND OF THE INVENTION

The present invention relates generally to a water supply decontamination system, and is particularly concerned with a decontamination system for water lines used in dental offices and other medical facilities.

Water supplies in all health care facilities have the potential for contamination by disease causing bacteria and viruses. The municipal water supply is known to carry certain bacteria, but the bacteria are usually present in such low numbers that they present no hazard. However, when such water is supplied to a dental water line, and stands in the line for extended periods, a bacterial biofilm forms on the plastic tubing due to the very high surface area to volume ratio of the tubing. The biofilm acts as a breeding ground for such disease producing bacteria as Pseudonomas, Klebsiella and Legionella. In addition, contamination also occurs from "suck-back" of fluids from the patient's mouth into the dental handpiece. As a result, water supplied from a dental water line to rinse a patient's mouth is often grossly contaminated and would not meet the standards required for municipal drinking water.

A fine aerosol mist is created by dental handpieces and the like, so that bacteria present in the water line are dispersed into the air and will be inhaled by both patient and dental personnel. This allows bacteria to enter the respiratory tract and has been shown to lead to infection or disease in some cases.

Another problem arising from the build-up of a biofilm in dental or other medically used water lines is that the biofilm is liable to spread back from the contaminated water line and into the building water supply lines. This has been shown to have occurred in some buildings, and such contamination is extremely difficult to eliminate.

The American Dental Association recommends flushing dental water lines for two minutes or more at the start of each day and before each patient. However, this has not proved to be sufficient to remove the source of contamination, which is the biofilm formed as a coating on the water line. Thus, after flushing, testing has shown that the dental unit water line water still regularly fails to meet the U.S. public health requirements for potable water (i.e. 500 C.F.U. s/ml).

Another solution which has been tried is to supply water to the lines from a sterile source, rather than using the municipal water supply. However, contamination of the line and water reservoir can still occur as a result of suck-back or retraction of fluids from the patient's mouth. Bacterial growth will be amplified as a result of the water standing in the line, and growth of a biofilm will eventually occur.

Another method which has been proposed to deal with this problem is to provide a bacterial filter on the delivery side of the water supply line. Again, this does not deal with the problem of the biofilm formed on the water supply line, and will itself become a source of patient cross-contamination if not changed frequently, due to bacterial growth directly on the filter. Additionally, although it serves as a barrier to suck-back contamination, bacteria caught on the filter from a patient's mouth may be flushed into the next patient's mouth. This is no different than if it merely flowed into the water lines.

Another approach is to disinfect the dental water line using sterilizing agents. However, this does not always eliminate the biofilm, from which bacteria break off and provide a source of contamination to water subsequently flowing through the line, and is inconvenient and time consuming with existing systems. Also, cross-contamination between patients is still possible.

Up to now, no effective and convenient method or system for effectively decontaminating dental and other water lines has been proposed. However, such a system is clearly needed in view of the potential for both patients and medical personnel to contract diseases as a result of contamination of such water lines.

SUMMARY OF THE INVENTION

It is an object of the present invention to provide a new and improved method and system for decontaminating water lines.

According to one aspect of the present invention, a water line decontamination system is provided, which comprises a water supply, a disinfectant supply, a source of pressurized gas such as air, and a selector valve assembly having a first inlet connected to the water supply, a second inlet connected to the disinfectant supply, a third inlet connected to the pressurized gas source, and an outlet for connection to the inlet of a water line. The selector valve assembly includes valves for selectively controlling the connection of the water supply, the disinfectant supply and the pressurized gas source to the outlet. In a preferred embodiment of the invention, the water supply and disinfectant supply each comprise a container or bottle for containing water and a suitable disinfectant liquid, respectively, and a selector valve is provided in the valve assembly for controlling the connection of the pressurized gas source to the two containers so as to selectively supply water or disinfectant under pressure to the outlet in run and flush conditions, respectively, of the system. The selector valve also controls the connection of the pressurized gas inlet directly to the outlet in a purge condition of the system.

With the selector valve in the "run" position, water is supplied to the water line on activation of a high speed drill, dental syringe, or other tool connected to the water line. Following a dental procedure, the selector valve member is moved to the "purge" position, in which pressurized air clears both unit water and patient source contaminated fluids from the dental line. The selector valve member is then moved to the "flush" position in which disinfectant flows into the dental line when the dental drill or syringe is activated. When disinfectant flows out of the dental tools the user knows that the water lines are full. The disinfectant is then allowed to stand in the line for a recommended sterilization time. The disinfectant may stand in the lines until the unit is used on the next patient or overnight. The selector valve is preferably biassed from the flush position back to the purge position, so that after each flush cycle the selector valve member is moved back to the purge position so that pressurized air flushes all disinfectant from the line. This ensures that an operator does not accidentally supply an unrestricted amount of disinfectant to the patient's mouth. After the line is purged, the valve member is moved to the run position to flush water through the line.

In the preferred embodiment, the water supply is a container of sterile water, however, the standard water supply may be used in conjunction with a sterile bacteria filter. A similar container of disinfectant is provided for the disinfectant supply, with each container selectively connected to the pressurized air source in order to supply water or disinfectant to the water line. The disinfectant is preferably colored so that the user can easily determine when the water lines are full of disinfectant. A bacterial filter acting as a biologic check valve may be located at the outlet of the selector valve assembly as a means of isolating the system from contamination within the water lines or from patients.

Any liquid sterilant may be used, such as chlorine, chlorox, chlorhexidine gluconate (Peridex), chlorine dioxide, ethanol, quaternary ammonium compounds, and the like. The sterilant may be of the type usable as a mouthwash, and may also be supplied to the patient's mouth to disinfect the oral cavity prior to or during a dental procedure. The CDC has recommended that anti-microbial pre-rinses will reduce the risk to staff of bacterial infection from patients during dental procedures.

According to another aspect of the present invention, a method of decontaminating water lines for connection to surgical or dental instruments is provided, which comprises the steps of connecting the water line to a supply of sterile water in a run operation during a medical or dental procedure, connecting the water line to a source of pressurized gas on completion of the procedure to purge water and contaminants from the water line in a purge operation, connecting the water line to a disinfectant supply after water has been purged from the line to flush disinfectant through the line in a flush operation, and allowing disinfectant to stand in the line for a predetermined time period.

After the predetermined time period, the line may be purged with pressurized gas or air for a sufficient time period to completely dry the line. It is then ready for re-filling with water. Alternatively, disinfectant may be run through the line again and even supplied to the patient's mouth where it is of the type suitable for use as a disinfecting mouthwash. A means of isolation of the system from water line contamination is also incorporated. The disinfectant which is supplied to the water line and left standing in the line may be a strong acid or strong base which is sufficiently caustic to break down any biofilm formed on the surface of the line or tube. The caustic disinfectant may be used periodically to stand in the line when the water line is not in use, for example overnight. This disinfectant is then flushed from the line before starting any patient procedure, after which the disinfectant inlet may be connected to a mouthwash type of disinfectant as described above.

A second alternative method is to purge the line with pressurized gas or air and thoroughly dry the lines for storage overnight. This dry environment eliminates the water stagnation which fosters biofilm growth. Desiccation may be as effective as chemical control to stop biofilm growth.

This decontamination system is easy and convenient to install on existing dental units using standard dental air lines and water lines. It provides an effective way for substantially reducing dental water line contamination. This will considerably reduce the risk of bacterial infection and transmission of other disease causing agents to both patients and dental or medical personnel.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
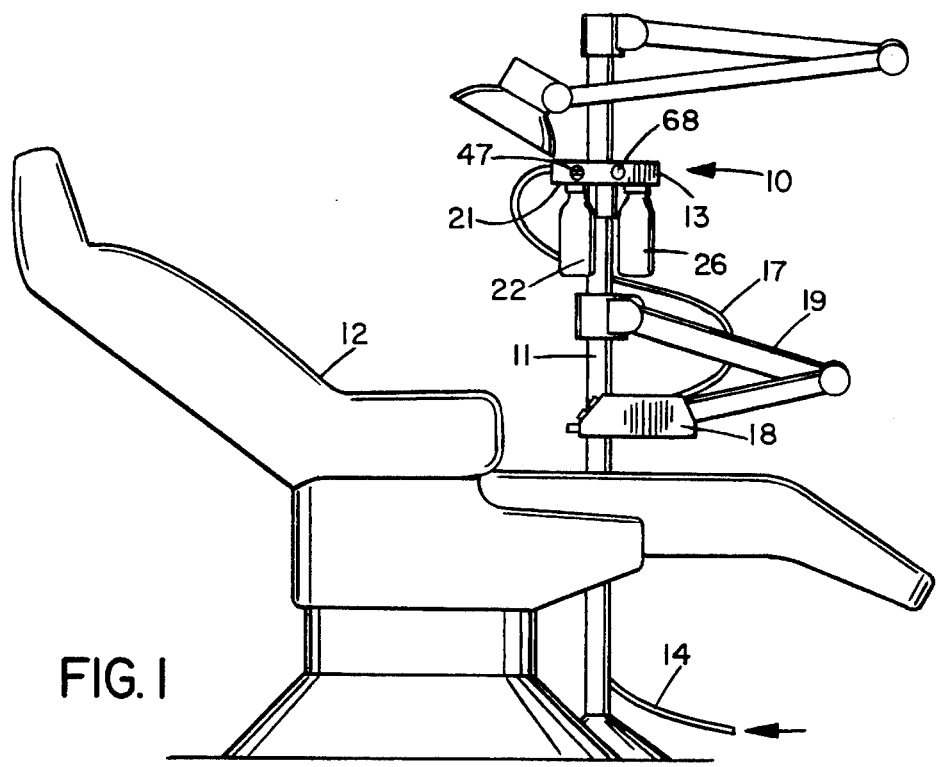
FIG. 1 is a side elevational view illustrating one possible installation of a decontamination unit according to a preferred embodiment of the invention on a dental chair unit.
Figure 2:
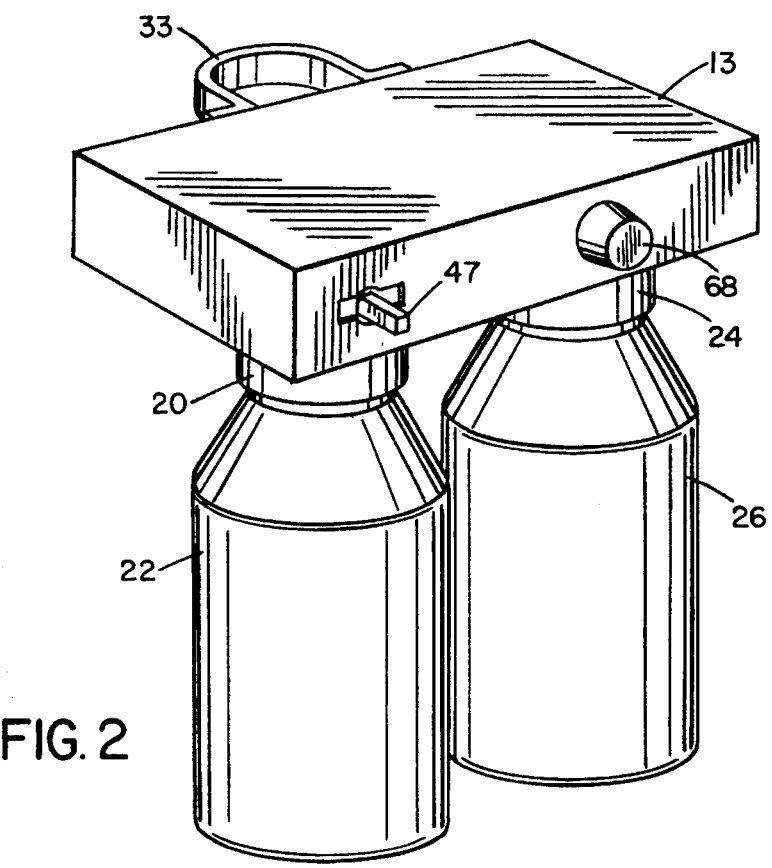
FIG. 2 is a perspective view of the decontamination unit.

FIG. 1 illustrates the water line decontamination unit 10 installed on a dental light supporting pole 11 of a dental chair unit 12. The unit 10 is designed for pole mounting or may alternatively be bolted to the undersurface of a dental cart unit carrying various dental tools, and plumbed into the existing water and air lines of the unit.

The unit 10 basically comprises an outer housing 13 designed for pole mounting or mounting on a dental cart unit, and having an air or gas inlet 14 for connection to a pressurized air supply, an air outlet 15 and water outlet 16 for connection to a dental water line 17. As illustrated in FIG. 1, line 17 is connected and incorporated into a dental tool unit 18 on articulating arm 19. The housing has a first adapter 20 in lower wall 21 for mounting a bottle 22 or other container for irrigating liquid such as sterile water, and a second adapter 24 for mounting a bottle 26 or other container for a selected disinfectant. Each adapter has an inlet 28,30, respectively, for pressurizing the container and an outlet 32,34 for flow of liquid from the container under pressure. The adapters preferably have threaded bores for receiving the threaded necks of bottles 22,26. A clamp ring 33 is provided for attaching the unit to a 2" round post, which is standard in the dental field. Screw holes (not illustrated) may be drilled in the top of housing 13 so that it can be attached via screws to the undersurface of a dental cart unit.

Figure 3:
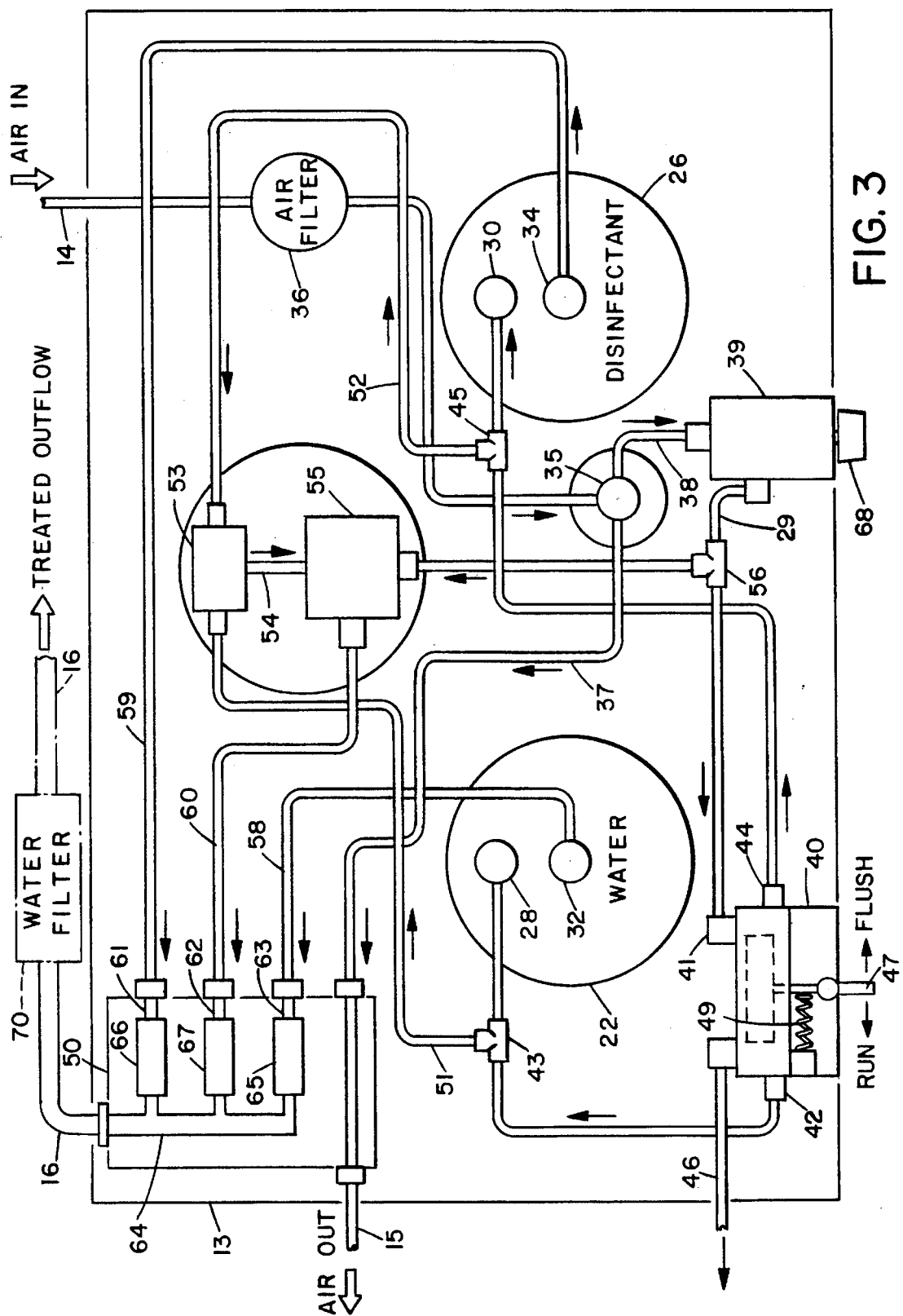
FIG. 3 is a block diagram illustrating the components of the decontamination unit and their interconnection.
Figure 4:
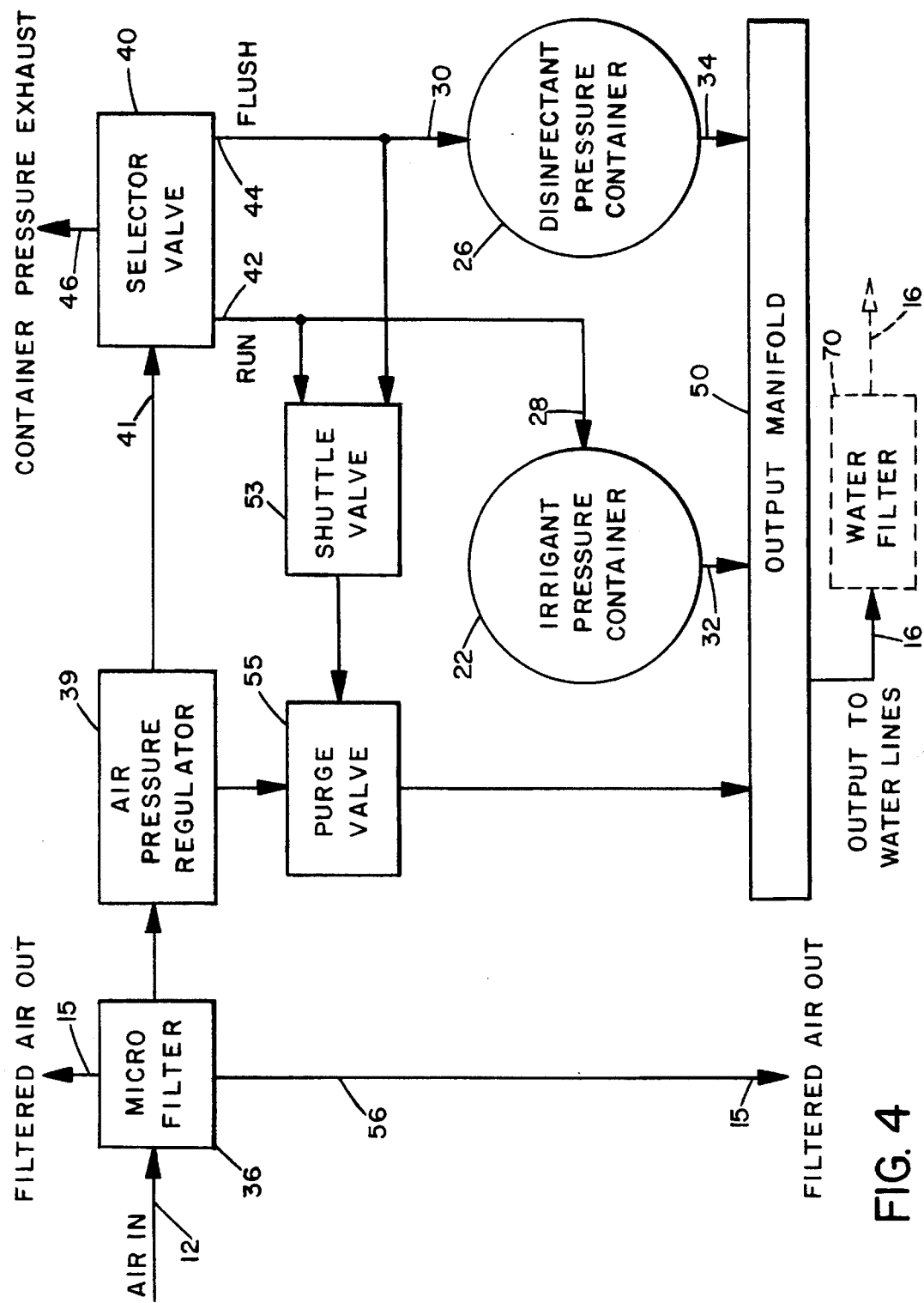
FIG. 4 is a schematic block diagram illustrating flow of gas and liquid through the unit.

As best illustrated in FIG. 3, the pressurized air inlet 14 is connected through a 0.01 micron air micro-filter 36 to a T-junction 35 having outlet lines 37 and 38. One outlet line 37 is connected through an outlet manifold 50 to an air outlet 15 for connection to the dental unit air line or to a three-way syringe. The other outlet line 38 is connected through air pressure regulator 39 and line 29 to the inlet 41 of a three position, four-way selector valve 40 for selectively connecting the air inlet 12 to one of two outlets 42 and 44. Selector valve 40 is preferably a normally open, three position, four-way, center vented toggle valve having a run position in which the air inlet 12 is connected to outlet 42, a flush position in which the air inlet is connected to outlet 44, and a purge position in which the inlet 41 is cut off and air is exhausted from the containers via an exhaust outlet 46. A toggle 47 on the front of the housing controls the position of the valve. A biassing spring 49 biasses the valve from the flush position to the purge position.

The outlets 42 and 44 are connected via T-junctions 43 and 45, respectively, to the pressurized air inlets 28 and 30, respectively, of the water and disinfectant pressure containers 22 and 26. The other outlets 51,52 respectively, from each of the T-junctions 43,45 are connected to opposite sides of a further shuttle valve 53. The outlet 54 of shuttle valve 53 is connected to an inlet of purge valve 55. Air line 29 also has a T-junction 56 connecting the line to purge valve 55. The shuttle valve 53 is an exhausting double check valve which is opened by pressure in either of the connecting lines from outlets 51 or 52, but which is closed when there is no pressure at either inlet.

Outlets 32 and 34 from the water and disinfectant containers 22,26 are each connected via lines 58,59 to output selector manifold 50 and from the manifold 50 to the housing outlet 16 to the water line. Purge valve 55 also has an output line 60 connected through manifold 50 to outlet 16. Valve 55 is a normally open, three-way pilot valve which is closed under pressure from either of the run or flush air lines 51 or 52.

The output selector manifold 50 is illustrated in detail in FIG. 3. Manifold 50 has three inlet passageways 61,62,63 connected in parallel to a single outlet passageway 64 in communication with the housing outlet 16. The inlet passageways 63,61,62 are connected to water run outlet line 58, disinfectant or flush outlet line 59, and purge valve or purge outlet line 60, respectively, and each passageway contains a check valve 65,66,67, respectively, which is normally closed.

Air from the dental unit supply enters the micro-filter which preferably filters the air to 0.01 micron. Filtered air flow continues through the air pressure regulator, which reduces the pressure to 30 p.s.i. The regulator pressure may be varied via control knob 68. The air supply from the air pressure regulator is connected to the selector valve and to the purge valve via T-junction 56.

The toggle 47 can be moved by the operator into any one of three possible valve positions: PURGE, RUN or FLUSH, and is biassed from the FLUSH position into the PURGE position, via spring 49, as illustrated in FIG. 3.

When the selector valve is in the PURGE position, no air flows out through the run or flush outlets of the selector valve. The purge valve will therefore be open and air will flow through the purge valve via line 60 to the manifold 50, forcing check valve 67 open so that pressurized air is supplied to the dental water line.

If the selector valve is moved to the RUN position, air input via line 41 will flow out of the run outlet 42 of the selector valve to the inlet 28 of the water container 22, and also to the purge valve via shuttle valve 53, closing the purge valve to cut off the air supply to the output manifold 50. The air will pressurize water container 22 to force water out via outlet 32, where it flows through line 58 and passageway 63 of the outlet manifold to the dental water line.

When the selector valve is moved to the FLUSH position, air will flow from inlet 41 through the selector valve to the flush outlet 44, supplying pressurized air to the inlet 30 of the disinfectant bottle 26 and simultaneously closing the purge valve 55. Disinfectant will flow out of the bottle 26 through outlet 34 and line 59 to the outlet manifold, opening check valve 66 and flowing through the manifold and via the outlet 16 to the dental water line. The toggle 47 must be held by the operator in the FLUSH position or it will be biassed back into the PURGE position automatically, cutting off the disinfectant supply. This is for safety reasons, and ensures that operators cannot accidentally leave the valve in the FLUSH position and supply unlimited disinfectant to the patient's mouth.

Thus, the system allows the operator to selectively run water or disinfectant through the water line 17, or to purge liquid from the line and replace it with pressurized air. This allows the water line to be disinfected and decontaminated at a precise disinfectant concentration quickly and easily between dental procedures, and provides a means for biofilm removal or control in the water line if properly used. In the preferred embodiment, a micro-filter 70 is provided at outlet 16 for filtering the water to 0.2 micron, isolating the valve housing from dental unit water line bacterial contamination by acting as a biologic check valve. Water may flow through but bacterial may not flow back through filter 70. The micro-filter 70 may be any suitable bacterial filter, such as the SteriLine cartridge developed by SciTech Dental of Bellevue, Wash., which filters out particles as small as 0.2 microns. Since the line is purged of liquid and dried before supplying disinfectant, the disinfectant concentration can be precisely controlled at rated levels, ensuring effective killing of bacteria.

A preferred method of using the system will now be described. The system is connected to a dental unit air supply at air inlet 14 at a point where it can be shut off via the delivery system master switch. Thus, the system is activated by turning on the dental office air compressor. The existing syringe air and water lines of the dental unit are disconnected and rerouted to the decontamination unit air outlet 15 and water outlet 16. When not in use, the toggle switch is left in the PURGE position. To fill the water lines, the switch is moved to the RUN position, supplying water from container 22 to the water lines as described above. After completion of a dental procedure, the switch is moved to the PURGE position, causing pressurized air to purge water from the water lines. This has the advantages of preventing further water line contamination from patient fluid suck-back and cross-contamination between patients, in addition to allowing follow on precise disinfectant concentration to be added to the lines. Once air can be felt coming from the exit end of the water line, the system has been purged and the switch is moved to the FLUSH position and held manually in that position. This supplies disinfectant at precise concentration from bottle 26 to the water line. When disinfectant flows out of any dental tool connected to the water line, the lines are full of disinfectant. The disinfectant may be colored to allow visual observation of when the lines are full. The air compressor may then be turned off and the toggle switch released, leaving the disinfectant standing in the water line for a predetermined decontamination period. The decontamination period will depend on the disinfectant being used, and may typically be around 10 minutes between patients. More thorough decontamination or sterilization may be achieved by allowing disinfectant to stand in line overnight (in excess of 10 hours). Alternatively, the line may be purged and left dry and empty overnight. This results in desiccation of any biofilm and would restrict further biofilm growth.

At the end of the sterilization period, the disinfectant is purged from the lines by turning on the air compressor with the toggle switch in the PURGE position.

The system is now ready for use again. The amount of disinfectant used for each flush cycle will depend on the total volume of tubing in the system. For example, a three handpiece cart unit with one three-way syringe will have about 30 feet of ⅛-inch diameter tubing. This will use about 2.5 ounces of disinfectant per flush cycle. After sterilizing the water lines, additional sterilant may be supplied to the patient's mouth to sterilize the oral cavity.

The unit may be connected to the office water supply rather than an independent supply of sterile water. In this case, a sterilizing means such as an additional 0.2 micron filter, flash heating unit, or ultra-violet sterilizing unit may be placed upstream of the unit in line with the water inlet. However, the system preferably uses commercially available bottles of sterile water or saline which can be screwed into the adapter on the housing unit as described above.

The water and disinfectant bottles are preferably transparent or translucent and may be graduated so that the fluid levels can be read directly by observation. When empty, the bottles are unscrewed from the adapters and refilled or replaced. The 0.2 micron filter or filters, if used, should be replaced daily. The disinfectant bottle can be filled with acid, bases, detergents and bioenzymes to remove biofilms, calcifications and other contaminants from the water lines periodically by specific protocol for maintenance purposes. One possible protocol would be to fill the line with chlorine bleach or 10% muratic acid once a week, and leave the unit overnight before purging the lines. The bottles are preferably plastic, screw-neck bottles which are rated to at least 100 p.s.i.

The water bottle may optionally be filled with a medicating solution instead of sterile water or saline for in-situ continuous irrigation of medication into surgical sites or into gingival sulci during periodontal root planning and standard dental cleanings to reduce or eliminate bacterial infection. Suitable medicating solutions are tetracycline, chlorhexidine, chlorine dioxide, iodine solutions and the like.

The dental line decontamination unit of this invention provides a means of limiting cross-contamination due to residual water or patient fluids in the delivery system or dental unit water lines. This system provides relatively sterile water or other fluids to the oral cavity of a patient during dental procedures, and considerably reduces the risk of any transmission of bacterial or viral infection to patient or dental personnel as a result of water line contamination. It is compact, relatively inexpensive, and easy to install and use adjacent to any dental or medical unit.

Although a preferred embodiment of the invention has been described above by way of example only, it will be understood by those skilled in the field that modifications may be made to the disclosed embodiment without departing from the scope of the invention, which is defined by the appended claims.

We claim:

1. A water line decontamination system, comprising:

a housing having a first inlet for connection to a pressurized gas source, a second inlet for connection to a supply of irrigating liquid, a third inlet for connection to a supply of disinfectant liquid, and an outlet for connection to a water line inlet;

a valve assembly in the housing for selectively connecting any one of said inlets to said outlet while disconnecting the other two inlets from said outlet; and control means for controlling said valve assembly to supply gas continuously from said first inlet to said outlet in a purge condition to purge liquid from a water line attached to said outlet and dry the water line to suppress biofilm development, said second and third inlets being disconnected from said outlet in said purge condition, to connect said irrigating liquid supply from said second inlet to said outlet in a run condition during normal use of said water line while said first and third inlets are disconnected from said outlet, and to supply disinfectant liquid from said third inlet to said outlet in a flush condition for disinfecting said water line, said first and second inlets being disconnected from said outlet in said flush condition.

2. A water line decontamination system, comprising:

a housing having a first inlet for connection to a pressurized gas source, a second inlet for connection to a supply of irrigating liquid, a third inlet for connection to a supply of disinfectant liquid, and an outlet for connection to a water line inlet;

a valve assembly in the housing for selectively supplying fluid from any one of said inlets to said outlet and disconnecting the other two inlets from the outlet;

control means for controlling said valve assembly to supply gas from said first inlet to said outlet in a purge condition to purge all liquid from a water line connected to said outlet and dry the water line to suppress biofilm development, to supply irrigating liquid from said second inlet to said outlet in a run condition during normal use of said water line, and to supply disinfectant liquid from said inlet to said outlet in a flush condition to disinfect said water line;

said housing having a first adapter for releasable connection to a first bottle for containing said irrigating liquid, and a second adapter for releasable connection to a second bottle for containing a disinfectant liquid, said second inlet being provided in said first adapter and said third inlet being provided in said second adapter, said first adapter having a first gas inlet for supplying gas to said first bottle and said second adapter having a second gas inlet for supplying gas to said second bottle, said valve assembly including valve means for selectively connecting said housing gas inlet to said first and second adapter gas inlets in said run and flush conditions, respectively.

3. The system as claimed in claim 2, wherein said valve assembly includes a three position selector valve having a gas inlet, a run outlet and a flush outlet, and a manual selector for selectively positioning the valve in a run position in which said valve inlet is connected to said run outlet, a flush position in which said valve inlet is connected to said flush outlet, and a purge position in which said run and flush outlets are both disconnected from said valve inlet, a first passageway in said housing connecting said housing first inlet to said valve gas inlet, a run passageway connecting said run outlet to said first adapter gas inlet, and a flush passageway connecting said flush outlet to said second adapter gas inlet.

4. The system as claimed in claim 3, including biassing means for biassing the selector valve from the flush position to the purge position.

5. The system as claimed in claim 3, including a purge valve for selectively connecting the first passageway to the housing outlet when the selector valve is in the purge position.

6. The system as claimed in claim 5, including control means for moving the purge valve between an open position connecting the first passageway to the housing outlet when the selector valve is in the purge position and a closed position cutting off the connection between said first passageway and housing outlet when the selector valve is in either the run position or the flush position.

7. The system as claimed in claim 6, wherein said control means comprises means for selectively connecting said purge valve to said run and flush passageways and for moving said valve into the closed position in response to gas pressure in either of said run and flush passageways.

8. The system as claimed in claim 2, including an outlet manifold in said housing having a single outlet connected to said housing outlet, and at least three inlets for selective connection to said manifold outlet, a first outlet passageway connecting said first, gas inlet to a first one of said manifold inlets, a second outlet passageway connecting said second inlet to a second one of said manifold inlets, and a third outlet passageway connecting said housing third inlet to a third one of said manifold inlets.

9. The system as claimed in claim 8, further including valve means in said first outlet passageway for connecting said housing gas inlet to said first manifold inlet only when said gas inlet is not connected to either of said adapter gas inlets.

10. The system as claimed in claim 8, wherein said manifold further includes a first check valve between said first manifold inlet and said outlet, a second check valve between said second manifold inlet and said outlet, and a third check valve between said third manifold inlet and said outlet, each check valve comprising means for selectively connecting the respective manifold inlet to the outlet in response to the presence of fluid under pressure at said manifold inlet.

11. The system as claimed in claim 1, wherein said housing has a gas outlet and an internal passageway connecting said gas inlet to said gas outlet.

12. The system as claimed in claim 11, wherein said housing has an additional passageway connecting said gas inlet to said water line outlet, and said valve assembly includes valve means in said additional passageway for selectively shutting off the connection from said gas inlet to said water line outlet when fluid is supplied to said water line outlet from either said second or said third inlet.

13. The system as claimed in claim 1, including a gas micro-filter at the first inlet.

14. A water line decontamination system, comprising:
- a housing having a first inlet for connection to a pressurized gas source, a second inlet for connection to a supply of irrigating liquid, a third inlet for connection to a supply of disinfectant liquid, and an outlet for connection to a water line inlet;
- a gas sterilizing means connected to said first inlet for sterilizing gas entering the housing;
- a water micro-filter connected at the water line outlet, the water micro-filter comprising a check valve for preventing passage of bacteria from the water line into the housing;
- a valve assembly for controlling the supply of gas, irrigating liquid and disinfectant liquid to the outlet, the valve assembly comprising valve means for connecting any one of said inlets to said outlet while disconnecting the other two inlets from said outlet;
- said valve assembly having a first, purge condition in which gas only is supplied from said gas inlet to said outlet to purge all liquid from the water line, replace the purged liquid with gas, and dry the line, whereby biofilm development is suppressed, said second and third inlets being disconnected from said outlet in said purge condition, a second, run condition during normal use of the water line in which irrigating liquid is supplied from said second inlet to said outlet while said first and third inlets are disconnected from said outlet, and a third, flush condition in which disinfectant liquid is supplied from said third inlet to said outlet to disinfect said water line while said first and second inlets are disconnected from said outlet; and
- a manual control device for controlling the operation of said valve assembly.

15. A water line decontamination system, comprising:
- an irrigating liquid supply;
- an irrigating liquid supply line connected to said supply of irrigating liquid;
- a disinfectant liquid supply;
- a disinfectant supply line connected to said supply of disinfectant;
- a pressurized gas source;
- a gas line connected to said pressurized gas source;
- an outlet line for connection to a water line;
- a connecting manifold connected to the irrigating liquid supply line, the disinfectant supply line, the gas supply line and the outlet line;
- a valve assembly for controlling the supply of irrigating liquid, disinfectant and gas to the irrigating liquid supply line, the disinfectant supply line, and the gas supply line, respectively, to supply fluid to only one of said lines at any one time, said valve assembly having a first, purge condition in which gas only is supplied via said gas line to said outlet line to purge any liquid from said water line connected to the outlet line and dry said water line to suppress biofilm development, a second, run condition in which irrigating liquid only is supplied via said irrigating liquid supply line to said outlet line during normal use of said water line, and a third, flush condition in which disinfectant liquid only is supplied via said disinfectant line to said outlet line to disinfect said water line; and
- manual control means for controlling the operation of said valve assembly.

16. The system as claimed in claim 15, including a unitary outer housing enclosing said irrigant supply line, disinfectant supply line and gas line, said connecting manifold and said valve assembly, said irrigating liquid supply comprising a bottle containing irrigating liquid, said disinfectant liquid supply comprising a bottle containing disinfectant liquid, said housing having a first adapter for releasable connection to said bottle containing irrigating liquid and a second adapter for releasable connection to said bottle containing disinfectant, each adapter having an outlet connected to said irrigating liquid supply line and disinfectant supply line, respectively.

17. The system as claimed in claim 16, wherein each of said adapters has a gas inlet for supplying gas to said bottle to force liquid out of said bottle into the connected supply line, said gas line being connected to each of said adapter gas inlets, and said valve assembly including a selector valve between said gas line and each of said adapter gas inlets to control the supply of gas to said inlets, the supply of gas to both inlets being cut off in said purge condition, the gas line being connected to said first adapter inlet only in said run condition, and the gas line being connected to said second adapter inlet in said flush condition.

18. The system as claimed in claim 17, including biassing means for biassing said selector valve from said flush to said purge condition.

19. The system as claimed in claim 17, wherein said valve assembly includes a purge valve in said gas line for controlling the supply of gas to said outlet line, said purge valve being movable between an open position in which gas is supplied to said outlet line and a closed position in which gas supply to said outlet line is cut off, and control means for moving said purge valve into said open position when the supply of gas to said adapter inlets is cut off and moving said purge valve into a closed position when gas is supplied to either of said adapter inlets.

20. A method of decontaminating a water line and reducing bacteriologically contaminated aerosols, comprising the steps of:
- connecting a first end of a water line to a valve unit for selectively connecting the water line to at least one of a supply of irrigating liquid, a supply of biofilm removing disinfectant of sufficient strength to break down biofilm when left in the line for a sufficient time period, and a pressurized gas supply, the water line having an opposite, second end for connection to an instrument;
- supplying sufficient disinfectant to the water line via the valve unit to fill the water line;
- leaving the disinfectant standing in the water line for a predetermined time period sufficient to break down biofilm formed in the water line;

at the end of the time period, supplying pressurized gas to the water line via the valve unit to purge the disinfectant from the second end of the water line;

after all disinfectant has been purged from the water line, irrigating liquid is supplied to the water line for use during a patient treatment period.

21. The method as claimed in claim 20, including the step of cutting off the supply of irrigating liquid and supplying pressurized gas to the water line at the end of the patient treatment period to purge irrigating liquid from the water line.

22. The method as claimed in claim 20, including supplying a precise concentration of disinfectant to the water line.

23. The method as claimed in claim 20, wherein the irrigating liquid supplied to the water line is an oral sterilizing solution.

24. The method as claimed in claim 20, comprising supplying irrigating liquid to the water line during a series of successive patient treatment periods, purging irrigating liquid from the water line after completion of each patient treatment period by supplying pressurized gas to the water line, supplying disinfectant to the water line and purging disinfectant from the water line before the next patient treatment period.

25. The method as claimed in claim 24, including the step of leaving the disinfectant standing in the water line for a first predetermined time period between successive patient treatment periods, and leaving the disinfectant standing in the water line for a second time period longer than said first predetermined time period at periodic intervals.

26. The method as claimed in claim 21 including the step of leaving gas in the water line for a predetermined time period longer than said first mentioned time period.

27. A method of decontaminating a water line, comprising the steps of:

connecting a water line to a valve unit for selectively connecting the water line to one of three separate fluid supplies, comprising a supply of irrigating liquid, a supply of disinfectant, and a supply of pressurized gas;

supplying irrigating liquid to the water line during successive treatment periods;

carrying out a water line disinfecting procedure between successive treatment periods; and when the water line is not in use for an extended time period, carrying out a maintenance procedure for suppressing biofilm growth in the water line;

the water line disinfecting procedure comprising the steps of:

supplying sufficient disinfectant to the water line to fill the water line;

leaving the disinfectant standing in the water line for a first predetermined time period for disinfecting the water line;

at the end of the time period, supplying pressurized gas to the water line to purge disinfectant from the water line and fill the water line with gas;

after disinfectant has been purged from the water line, supplying irrigating liquid to the water line during the next treatment period;

after the treatment period, supplying pressurized gas to the water line for a second time period to purge the liquid from the water line;

the water line maintenance procedure comprising purging liquid from the water line and leaving gas standing in the water line for a predetermined time period longer than said first time period to dry the water line and suppress biofilm development in the water line.

28. The method as claimed in claim 20, including the step of connecting the water line to a supply of oral sterilizing liquid after the step of supplying pressurized gas to the water line, and supplying said oral sterilizing liquid to a patient's oral cavity at the start of a patient treatment period to disinfect the oral cavity.

29. The method as claimed in claim 20, including the step of sterilizing said irrigating liquid prior to supplying said sterilized irrigating liquid to said water line.

30. The method as claimed in claim 20, including the step of micro-filtering said pressurized gas prior to supplying said gas to said water line.

31. The method as claimed in claim 20, including the step of connecting a water micro-filter between the output of the valve unit and the input of the water line to isolate the valve unit from bacteria in the water line.

32. The method as claimed in claim 20, including the step of connecting the water line to a supply of a second, different disinfectant from said biofilm removing disinfectant during a series of patient treatments, said second disinfectant comprising a sterilizing solution suitable for use in the oral cavity, supplying pressurized gas to the water line to purge irrigating liquid from the water line after completion of each patient treatment, after irrigating liquid has been purged from the water line, supplying said second disinfectant to the water line, and allowing said second disinfectant to stand in the water line for a second time period before the next patient treatment.

33. The method as claimed in claim 32, including the step of purging said second disinfectant from the water line before supplying irrigating liquid to the water line for the next patient treatment.

34. The method as claimed in claim 20, wherein said steps of supplying biofilm removing disinfectant to the water line, allowing the disinfectant to stand in the water line for a predetermined time period, and purging the disinfectant from the water line, comprise a maintenance procedure performed during extended periods when said water line is not in use or in case of water line recontamination, and said method further includes a line disinfecting procedure between each pair of successive patients in a series of successive patient treatments, the line disinfecting procedure comprising the steps of supplying pressurized gas to purge irrigating liquid from the water line at the end of each patient treatment, supplying a second disinfectant comprising an oral sterilizing solution to the water line after all irrigating liquid has been purged from the water line, and allowing said second disinfectant to stand in the water line for a second time period before the next patient treatment, the second time period being shorter than said first mentioned time period.

35. A method for reducing production of bacteriologically contaminated aerosols at a medical handpiece connected to a water line for supply of irrigating liquid to the handpiece, comprising the steps of:

providing a supply of pressurized gas, a supply of sterilized irrigating liquid, and a supply of disinfectant liquid;

connecting the pressurized gas supply, the irrigating liquid supply and the disinfectant liquid supply to a valve unit for connecting only one of the supplies at any one time to a water line;

connecting a micro-filter between the valve unit and the water line to isolate the valve unit from any bacteria in the water line;

during each of a series of patient treatment periods, controlling the valve unit to connect the irrigating liquid supply to the water line;

between each successive pair of patient treatment periods, disconnecting the irrigating liquid supply and connecting the water line to the pressurized gas supply to supply gas to the water line and purge all of the irrigating liquid from the water line;

after purging all irrigating liquid from the water line, controlling the valve unit to connect the disinfectant liquid to the water line and supplying sufficient disinfectant to the water line to fill the water line;

leaving the disinfectant liquid standing in the water line for a predetermined time period sufficient to disinfect the water line;

connecting the pressurized gas supply to the water line via a gas micro-filter at the end of the predetermined time period to purge disinfectant from the water line; and at the end of a series of patient treatment periods, connecting the pressurized gas supply to the water line, supplying gas to the water line to purge liquid from the water line and drying the water line to suppress biofilm development while the water line is not in use.

* * * * *